United States Patent [19]

Voelger et al.

[11] 4,331,687
[45] May 25, 1982

[54] TREATMENT OF PARKINSON'S DISEASE

[75] Inventors: Karl-Dieter Voelger, Bickenbach; Ilse Treudler, Messel, both of Fed. Rep. of Germany

[73] Assignee: Röhm Pharma GmbH, Weiterstadt, Fed. Rep. of Germany

[21] Appl. No.: 240,161

[22] Filed: Mar. 3, 1981

[30] Foreign Application Priority Data

Mar. 8, 1980 [DE] Fed. Rep. of Germany ....... 3008993

[51] Int. Cl.³ .......................................... A61K 31/135
[52] U.S. Cl. .................................................. 424/330
[58] Field of Search ........................................ 424/330

[56] References Cited

U.S. PATENT DOCUMENTS 2,997,422  8/1961  Tedeschi ............................ 167/65

FOREIGN PATENT DOCUMENTS 2512893  10/1975  Fed. Rep. of Germany .

OTHER PUBLICATIONS

Chem. Abst., 9th Coll. Index, p. 13066cs, Chem. Substances—Copper, bis(methyl-Diazecinone.
Chem. Abst., vol. 78, (1973)—79770t.
Chemical Abstracts 84, 8944r.
S. H. Snyder, J. Psychiatr. Res. 10, 153, (1974).
A. S. Horn et al., J. Pharmacol. Exper. Ther. 180, 523-530, (1972).
S. H. Snyder et al., in "L-DOPA and Behavior", E. Malitz and Sidney, Raven Press, 1972, pp. 35-56.
Chem. Abstracts 76, 81304w, (1972).
Riederer et al., Abstract #586, 8th Intl. Congress of Pharmacology, Tokyo, Jul. 19-24, (1981).

Primary Examiner—Stanley J. Friedman
Attorney, Agent, or Firm—Curtis, Morris & Safford

[57] ABSTRACT

What is disclosed is a method for the treatment of Parkinsonism or of psychic disturbances in a patient suffering therefrom, which method comprises orally or parenterally administering to said patient an effective amount of an active agent selected from the group consisting of (+)-trans-2-phenylcyclopropyl amine and physiologically acceptable acid addition salts thereof, said agent being essentially free of the corresponding (−)-enantiomer and its salts.

5 Claims, No Drawings

TREATMENT OF PARKINSON'S DISEASE

The present invention relates to the use of (+)-trans-2-phenylcyclopropyl amine for the treatment of Parkinsonism and as a geriatric agent.

The therapeutic use of (−)-trans-2-phenylcyclopropyl amine for the temporary lessening of symptoms of depression, without significant side effects in humans, and a corresponding composition are known in the art. This prior art stresses the requirement that the compositions must be essentially free of (+)-trans-2-phenylcyclopropyl amine.

It is also known that the trans-isomers of 2-phenylcyclopropyl amine (tranylcypromine) act as an inhibitor of the enzyme monoaminoxidase, found in the body.

It has further been determined that the (+)-enantiomer of tranylcypromine has a monoaminoxidase-effect which is from 15 to 20 times greater than that of the (−)-enantiomer. However, on the other hand, the (−)-enantiomer is a many times better inhibitor of catecholamine uptake in the brain synaptosomes than is the (+)-enantiomer.

Since a clincial comparison existed of the unambiguous superiority of the (−)-enantiomer of tranylcypromine as an antidepressive agent coupled with reduced side effects, in comparison with (+)-enantiomer, the conception arose that the antidepressive effect of the compound was attributable to the inhibiting effect towards catecholamine uptake in the brain synaptosomes. [cf. S. Snyder et al., J. Pharmac. Exp. Therapeutics 180, (3) (1972), S. Snyder et al., "L-Dopa Behaviour", pages 35–56, Ed. Malitz, Raven Press 1972; S. H. Snyder, J. Psychiatr. Res. 10, 153 (1974)].

From this point of view, an exclusion of the use of (+)-trans-2-phenylcyclopropyl amine from therapy follows as a result, as this indeed has occurred in the prior art first mentioned herein.

It has now been found that Parkinson's disease (morbus Parkinson) can be treated with good result if (+)-trans-2-phenylcyclopropyl amine or a physiologically acceptable acid addition salt thereof is used as an active agent.

Parkinson's disease shows a number of symptoms, which can be divided into three groups:
(1) motor disturbances [with plus-symptoms, such as increases in the tone of the striated musculature (rigor) as well as tremor, and minus-symptoms such as decrease in overall motor reflexes (akinesia) and loss of the attitudinal reflex];
(2) vegetative symptoms (increased flow of saliva and tears), and
(3) psychic disturbances (decision-making difficulties, depressed mood, inter alia.).

The degenerative decrease of nerve cells in the motor core-regions of the brain stem are held responsible for these difficulties, which mostly begin between the 40th and 60th year.

It appears further that the administration of (+)-trans-2-phenylcyclopropyl amine and its acceptable acid addition salts in general combats with surprising success those psychic disturbances mentioned under (3) above, further including loss of drive and symptoms of depression which as a rule first are manifest in old age but which can also appear earlier.

Thus, administration of this active agent according to the invention also includes a geriatric effect.

A rational preparation of trans-2-phenyl-cyclopropyl amine is described, for example, in U.S. Pat. No. 4,016,204. Separation into the (+) or the (−)-enantiomers of tranylcypromine is described, for example, by Kaiser in the Journal of Medicinal and Pharmaceutical Chemistry 5, 1243 (1962).

The racemate which is obtained in the preparation of trans-2-phenylcyclopropyl amine can be worked up by classical methods for the racemic separation of optically active amines, i.e. by salt formation with optically active acids such as tartaric acid. [cf. Houben-Weyl, Vol. IV, Part II, pages 513–519, George Thieme Verlag (1955)].

As physiologically or pharmaceutically acceptable acid addition salts of (+)-tranylcypromine, salts of inorganic acids such as of sulfuric, nitric, phosphoric, and hydrochloric acid, but also those of organic acids such as acetic, propionic, succinic, fumaric, maleic, citric, tartaric, cinnamic, p-aminobenzoic, p-aacetaminobenzoic, salicylic, acetylsalicylic, lactic, mandelic, and ethandisulfonic acid, inter alia, are used according to the present invention. The preparation of acid addition salts can occur in the manner known in the art, for example by solution of the free (+)-tranylcypromine in a suitable solvent and addition of the desired acid, for example in a stoichiometric ratio, and isolation of the acid addition salt which is formed.

As solvents, alcohols such as ethanol and methanol, ketones such as acetone and methylisopropyl ketone, ethers such as diethyl ether and dioxane, esters such as ethyl acetate, (aqueous) acids such as acetic acid, hydrochloric acid, and sulfuric acid, as well as combinations of such solvents, in addition to water, can be considered.

The preparations according to the invention can contain pharmaceutically acceptable carriers and auxiliaries. Further, they can be combined with other active ingredients. However, the precautions pertinent to monoaminooxidaseinhibitors (thymeretika) must be strictly observed. In particular, the administration and consumption of amines, for example those contained in food, must be carefully controlled.

The simultaneous administration of sympathomimetic amines is to be avoided. Likewise, food which contain large amounts of biogenic amines which increase blood pressure, such as cheese, present a potential danger.

The pharmaceutical compositions according to the invention can be administered parenterally and enterally. They can be prepared in the conventional way using the common carriers, auxiliaries, and solvents. Dosage forms for oral administration are preferred. Solid compositions suitable for oral administration, such as tablets, capsules, dragees, etc. represent one embodiment of the invention. For oral administration, pharmaceutically indifferent solid substances such as mannitol, milk sugar, organic or inorganic calcium salts, etc, can be used as carriers. The amount of solid carriers used in this embodiment can be widely varied. For example, the use of about 25 mg to 1 g of a solid carrier is suitable.

As binders, polyvinyl pyrrolidone, gelatin, or cellulose derivatives, inter alia, come into consideration. As further additives, tablet dissolving agents, such as starch or alginic acid, lubricants such as stearic acid or its salts, and inorganic flow agents such as talc or colloidal salicylic acid, as well as agents for altering taste, can be employed as further additives.

The active (+)-tranylcypromine or its acid addition salts can be mixed with the auxiliaries in the conventional fashion and can be granulated wet or dry. According to the kind of auxiliary substance used, a powder which can be converted directly into tables can optionally also be obtained. The granulate or powder can be filled directly into capsules or pressed into tablet cores in the conventional way.

Also, administration using ampules and suppositories comes into consideration. The dosages for the pharmaceutical preparation according to the invention depend on the nature and gravity of the disease, the age and disposition of the patient, as well as other individual factors which must be taken into consideration in the usual way.

The dosage preferably administered is in the range from 0.1 mg to 100 mg per day, preferably from 0.1 to 20 mg per day, and especially from 0.1–10 mg/day of the active ingredient, (+)-tranylcypromine, or corresponding quantities of the acid addition salts in the therapy of Parkinson's disease. There seems to be no direct relationship between the body weight of the patient and the effect of the drug against Parkinsonism. Administration can take place one to about four times a day, depending on the pharmaceutical formulation which is found adequate.

The outstanding suitability of (+)-tranylcypromine for combatting the Parkinson syndrome has been clinically confirmed.

Tranylcypromine can also be administered in combination with other drugs, for example with L-dihydroxyphenylalanine (L-dopa). The possibility of thus further prolonging the efficacy of treatment with L-dopa beyond the time limit heretofore inevitably encountered with the administration of pure L-dopa because of non-functioning of the L-dopa receptors is particularly interesting.

A better understanding of the invention and of its many advantages will be had from the following Examples, given by way of illustration.

EXAMPLE 1

(a) Preparation of capsules containing (+)-tranylcypromine sulfate
  (a) Preparation of the active ingredient The active agent is ground in a mill.
  (b) Capsule fill/recipe

| | |
|---|---|
| (+)-trans-2-phenyl-cyclopropylamine sulfate | 4.04 g |
| magnesium stearate | 0.50 g |
| lactose [Deutsches Arzneibuch (German Pharmacopoeia)] | 95.46 g |
| | 100.00 g |

All components are mixed with a mechanical mixer. The mixture is sieved with a sieve having mesh openings of 0.06 mm.

(c) Capsule preparation

The aforementioned mixture is filled into hard gelatin capsules, Size 4, using a capsule filling machine. The fill weight is 170 mg. One capsule contains 6.87 mg of active ingredient.

EXAMPLE 2

Preparation of ampules containing (+)-tranylcypromine hydrochloride

For parenteral administration, 2.0 mg of (+)-trans-2-phenyl-cylopropylamine hydrochloride and 0.375 mg of sodium chloride are readily dissolved in 10 ml of water to provide an injectable dose.

The solution can be filled into ampules which are then sealed.

What is claimed is:

1. A method for the treatment of Parkinsonism in a patient suffering therefrom, which method comprises orally or parenterally administering to said patient an effective amount of an active agent selected from the group consisting of (+)-trans-2-phenylcyclopropyl amine and physiologically acceptable acid addition salts thereof, said agent being essentially free of the corresponding (−)-enantiomer and its salts.

2. A method as in claim 1 wherein a dose of 0.1 mg to 100 mg of (+)-trans-2-phenylcyclopropyl amine, or a corresponding amount of an acid addition salt thereof, is administered per day to said patient.

3. A method as in claim 1 wherein a dose of 0.1 mg to 20 mg of (+)-trans-2-phenylcyclopropyl amine, or a corresponding amount of an acid addition salt thereof, is administered per day to said patient.

4. A method as in claim 1 wherein said active agent is orally administered.

5. A method as in claim 1 wherein said active agent is parenterally administered.

* * * * *